United States Patent [19]

Penco et al.

[11] 4,216,157
[45] Aug. 5, 1980

[54] SUBSTITUTED ANTITUMOR ANTHRACYCLINES

[75] Inventors: Sergio Penco, Milan; Fausto Gozzi, Zola Predosa; Francesco Angelucci, Milan; Federico Arcamone, Nerviano, all of Italy

[73] Assignee: Farmitalia Carlo Erba S.p.A., Milan, Italy

[21] Appl. No.: 33,994

[22] Filed: Apr. 27, 1979

Related U.S. Application Data

[62] Division of Ser. No. 941,847, Sep. 13, 1978.

[30] Foreign Application Priority Data

May 9, 1978 [IT] Italy .................... 23151 A/78

[51] Int. Cl.² ........................... C07C 49/72
[52] U.S. Cl. .................................. 260/365
[58] Field of Search ........................ 260/365

[56] References Cited

U.S. PATENT DOCUMENTS

| | | | |
|---|---|---|---|
| 3,201,424 | 8/1965 | McCormick et al. | 260/365 |
| 3,665,018 | 5/1972 | Jolles | 260/365 |
| 3,686,163 | 8/1972 | Arcamone et al. | 260/365 |
| 3,963,760 | 6/1976 | Bernardi et al. | 260/365 |

Primary Examiner—Winston A. Douglas
Assistant Examiner—Raymond K. Covington
Attorney, Agent, or Firm—Hubbell, Cohen, Stiefel & Gross

[57] ABSTRACT

Compounds having the formula:

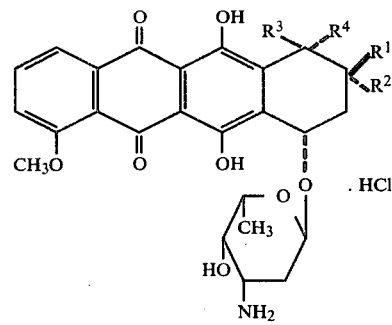

wherein
(a) when $R^1$ is —COCH₃ or —COCH₂OH, $R^2$ is —OH, $R^3$ is —OCH₃ and $R^4$ is —H;
(b) when $R^2$ is —COCH₃ or —COCH₂OH; $R^1$ is —OH, $R^3$ is —H and $R^4$ is —OCH₃;

and which are useful in treating certain mammalian tumors, are prepared from 9,10-anhydro-N-trifluoroacetyl daunorubicin, a known compound.

2 Claims, No Drawings

SUBSTITUTED ANTITUMOR ANTHRACYCLINES

The invention described herein was made in the course of work under a grant from the United States Department of Health, Education and Welfare.

CROSS REFERENCE TO RELATED APPLICATIONS

This is a division of application Ser. No. 941,847, filed Sept. 13, 1978.

BACKGROUND OF THE INVENTION

1. Field of the Invention

The present invention relates to new antitumor glycosides of the anthracycline series, novel intermediates used for making them, processes for the preparation of said glycosides and the use thereof.

2. The Prior Art

Daunorubicin (also known as daunomycin) and doxorubicin (also known as adriamycin), of which the present compounds are derivatives, are known and are known to be useful in treating certain mammalian tumors.

The compound 9,10-anhydro-N-trifluoroacetyl-daunorubicin (X), which is the starting material for the compounds of the present invention is a known compound which is described in British Patent Specification No. 53456/76, owned by the unrecorded assignee hereof.

SUMMARY OF THE INVENTION

The present invention provides, in one aspect thereof, a new class of antitumor anthracyclines of the formula:

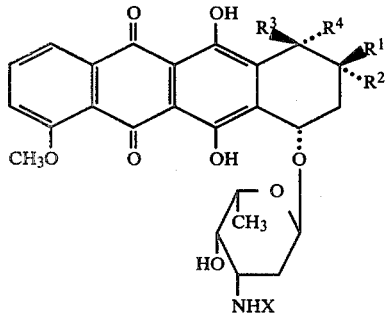

I: $R^1=COCH_3$; $R^2=OH$; $R^3=OCH_3$; $R^4=H$; $X=COCF_3$;
II: $R^1=COCH_3$; $R^2=OH$; $R^3=OCH_3$; $R^4=H$; $X=H$;
III: $R^1=COCH_2OH$; $R^2=OH$; $R^3=OCH_3$; $R^4=H$; $X=H$;
IV: $R^1=OH$; $R^2=COCH_3$; $R^3=H$; $R^4=OCH_3$; $X=COCF_3$;
V: $R^1=OH$; $R^2=COCH_3$; $R^3=H$; $R^4=OCH_3$; $X=H$;
VI: $R^1=OH$; $R^2=COCH_2OH$; $R^3=H$; $R^4=OCH_3$; $X=H$.

Among these six compounds, the four (II, III, V and VI) wherein X is H are the most important.

The invention also provides, in another aspect, a novel method for preparing these compounds utilizing several novel intermediates, which are also within the scope of the invention.

In yet another aspect, the invention provides pharmaceutical compositions which include the novel antitumor compounds of the invention.

Finally, the invention also provides a method of using the novel antitumor compounds of the invention in the treatment of certain mammalian tumors.

The preparation of the compounds of formulae I–VI is based on the synthesis of the tetracyclic aglycones of the formula:

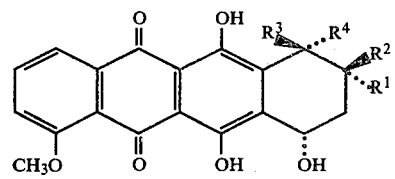

VII: $R^1=OH$; $R^2=COCH_3$; $R^3=OCH_3$; $R^4=H$;
VIII: $R^1=COCH_3$; $R^2=OH$; $R^3=H$; $R^4=OCH_3$;

and on the subsequent condensation of the aglycones VII and VIII with the known halosugar, 1-chloro-N,O-trifluoroacetyldaunosamine (IX):

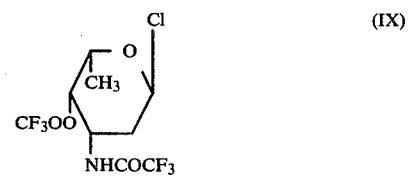

to form the corresponding N,O protected glycosides, which after treatment with methanol to eliminate the O-protecting trifluoroacetyl group, form the corresponding N-protected glycosides I and IV. After hydrolysis of the N-trifluoroacetyl-protecting group on the sugar moiety, 10-methoxydaunorubicin (II) and 9,10-diepi-10-methoxydaunorubicin (V) are obtained. The corresponding doxorubicin analogs (III) and (VI) are prepared from (II) and (V), respectively, via the 14-bromo derivatives, in accordance with the method described in U.S. Pat. No. 3,803,124 which is owned by the unrecorded assignee hereof. The starting materials for the preparation of the new glycosides (I–VI) of the invention therefore, are the anthracyclinones (VII) and (VIII) which were previously unknown. The novel anthracyclinones (VII) and (VIII) are synthesized, starting from 9,10-anhydro-N-trifluoroacetyldaunorubicin (X), which is described in British Patent specification No. 53456/76 (owned by the unrecorded assignee hereof). The synthetic reaction scheme is set forth below:

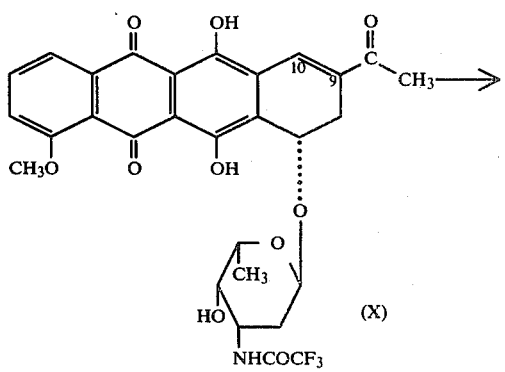

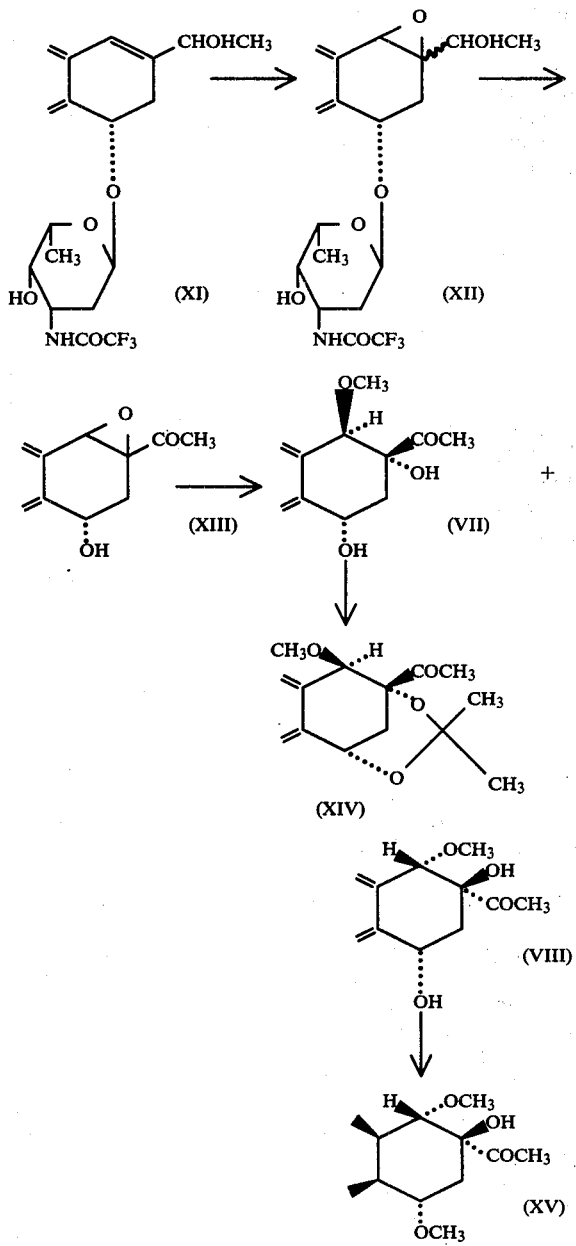

In order to effect epoxidation of the conjugated double bond present at the C-9, C-10 position in (X), it is first necessary to reduce the keto function to the corresponding α,β-unsaturated alcohol (XI). This reduction is effected using sodium cyanoborohydride in a suitable water-miscible-organic solvent, such as dioxane or dimethoxyethane, in the presence of a mineral acid, and yields quantitatively the corresponding 13-dihydroderivative (XI). Compound (XI) is then subjected to an expoxidation reaction using -chloroperbenzoic acid in an aprotic solvent, such as methylene chloride, chloroform or acetone. The epoxidation reaction proceeds at a temperature between 25° and 80° C. to give 9,10-epoxide-13-dihydro-N-trifluoroacetyldaunorubicin (XII), as an epimeric mixture. The regeneration of the keto function, with the contemporaneous cleavage of the glycosidic linkage, is performed by oxidation with dimethyl sulfoxide and dicyclohexylcarbodiimide, using pyridinium trifluoroacetate as a catalyst. The course of this oxidation reaction is influenced by the amount of catalyst; using the ratio of substrate to salt of 1:1, compound (XIII) is obtained in high yield. The subsequent introduction of the methoxy group, which is performed by opening of the oxirane ring of compound (XIII) with methanol, in the presence of a catalytic amount of p-toluenesulfonic acid, gives, in the approximate ratio of 7:2, a mixture of the aglycones (VII) and (VIII) which are separated by chromatography on silica gel. Compounds (VII) and (VIII) differ stereochemically at the C-9 and C-10 centers. This is demonstrated by the fact that only compound (VII) forms a 7,9-isopropylidenderivative (XIV) by treatment with 2,2-dimethoxypropane, which shows that the hydroxyl groups at C-7 and C-9 are cis. The pmr spectra of (VII) and (VIII) show that the C-10 H has an equatorial orientation in (VII) and an axial orientation in (VIII). Treatment of (VIII) with 2,2-dimethoxypropane gives 7-methoxy-9,10-diepi-10-methoxydaunomycinone (XV).

The coupling reaction between the aglycones (VII) and (VIII) and the N,O protected halosugar (IX) to form the glycosidic linkage, is carried out in a suitable organic solvent, such as chloroform, methylene chloride or tetrahydrofuran in the presence of a silver salt as catalyst. The thereby obtained N,O protected glycosides are first treated with methanol to eliminate the O-protecting trifluoroacetyl group on the sugar moiety, to give the N-protected glycosides (I) and (IV). These compounds, upon mild alkaline treatment, are converted in quantitative yield to 10-methoxydaunorubicin (II) and 9,10-diepi-10-methoxydaunorubicin (V), respectively.

The corresponding doxorubicin analogs (III) and (VI) are respectively obtained from (II) and (V) via the 14-bromo derivatives, according to the procedure described in U.S. Pat. No. 3,803,124. The new compounds (I–VI) display antimitotic activity and are therefore useful therapeutic agents for the treatment of tumor diseases in mammals.

DESCRIPTION OF THE PREFERRED EMBODIMENTS

The following examples are given to better illustrate the invention without, however, being a limitation thereof.

EXAMPLE 1

9,10-Anhydro-13-dihydro-N-trifluoroacetyldaunorubicin (XI)

6.0 Grams (10 mmoles) of 9,10-anhydro-N-trifluoroacetyl daunorubicin (X) were dissolved in 2000 ml. of methanol. The solution was acidified with 50 ml. of 0.1 N aqueous hydrochloric acid and then reacted with an aqueous solution of NaCNBH$_3$ (4.0 g. in 200 ml. of H$_2$O). The reaction mixture was stirred at room temperature for 48 hours, while keeping the pH below 4 by the addition of 0.1 N aqueous hydrochloric acid. After neutralization with an excess of solid NaHCO$_3$, the solution was evaporated to a residue under vacuum and the residue, after being dissolved in chloroform, was washed with water. The chloroform solution was dried over anhydrous Na$_2$SO$_4$ and the solvent finally removed under vacuum to yield crude 9,10-anhydro-13-dihydro-N-trifluoroacetyldaunorubicin (XI). Pure 9,10-anhydro-13-dihydro-N-trifluoroacetyldaunorubicin (XI) was obtained by chromatographic purification on a column of silicic acid using as the eluting agent the system $CHCl_3:(CH_3)_2CO$ (95:5 v/v). The pure compound melts at 165° C. (dec.). Visible spectrum ($CHCl_3$) maxima at 520, 556 nm.

EXAMPLE 2

9-Deoxy-9,10-epoxide-13-dihydro-N-trifluoroacetyl-daunorubicin (XII)

To a solution of 8 g. (3.28 mmoles) of 9,10-anhydro-13-dihydro-N-trifluoroacetyldaunorubicin (XI) in 400 ml. of chloroform, there were added 1.08 g.; 6 mmoles of m-chloroperbenzoic acid, and the reaction mixture was warmed at 80° C. for 3 hours. The initial cherry color of the solution gradually changed to red. The reaction solution was then cooled and washed with an aqueous saturated solution of $NaHCO_3$, and then with water, after which it was finally dried over anhydrous $Na_2SO_4$. The solvent was evaporated to a residue under vacuum. The residue (2.0 g.), which exhibited, in the visible spectrum ($CHCl_3$), maxima at 490, 504 and 540 mµ is in agreement with what would be expected as a result of the disappearance of the double bond at the C-9, C-10 position of (XI), was a mixture of epimeric epoxides and was used without further purification in the following example.

EXAMPLE 3

9-Deoxy-9,10-epoxide-daunomycinone (XIII)

To a stirred solution of 3.85 g. (6 mmoles) of 9-deoxy-9,10-epoxide-13-dihydro-N-trifluoroacetyldaunomycin (XII) under a nitrogen atmosphere, in 100 ml. of anhydrous dimethylsulfoxide, there were added, one after the other, 3.8 g. (18 mmoles) of dicyclohexylcarbodiimide, 0.5 ml. (6 mmoles) of anhydrous pyridine and 0.23 ml. (3 mmoles) of trifluoroacetic acid. The resulting mixture was stirred at room temperature for 15 hours and then diluted with 500 ml. of chloroform. The chloroform solution was thoroughly washed with water, dried and evaporated to a residue. The residue was taken up in ethyl acetate, the insoluble dicyclohexylurea was filtered off and the filtered solution evaporated to a residue to give 9-deoxy-9,10-epoxide-daunomycinone (XIII) in quantitative yield.

IR: 1720 $cm_{\overline{v}}^{-1} C=O$; 1580 and 1620 $cm_{\overline{v}}^{-1} C=O$ quinone NMR ($CDCl_3$): at 2.27 (1, $CH_3$—C=O); 4.10 (s, $OCH_3$) and 4.18δ (1, H-10).

EXAMPLE 4

10-Methoxy-daunomycinone (VII) and 9,10-diepi-10-methoxy-daunomycinone (VIII)

A solution of 4.3 g. of 9-deoxy-9,10-epoxide-daunomycinone (XIII) in 500 ml. of anhydrous methanol was warmed at reflux temperature for 15 hours in the presence of a catalytic amount of p-toluensulfonic acid. The reaction mixture was then cooled and evaporated to a residue which was then dissolved in 300 ml. of chloroform, washed with an aqueous 5% solution of $NaHCO_3$, water, dried over anhydrous $Na_2SO_4$ and again evaporated to a residue. The thusly obtained crude material was a mixture of compounds (VII) and (VIII) in the approximate ratio of 7:2. The mixture was chromatographed on a column of silicic acid using the mixture ethylacetate-toluene-petroleum ether (3:2:2 v/v) as the eluting agent. Pure 10-methoxydaunomycinone (VII): (1.5 g.) and 9,10-diepi-10-methoxydaunomycinone (VIII): (0.42 g.), 72% overall yield, were obtained. 10-Methoxydaunomycinone (VII): m.p. 220° C. (dec.); $[α]_D^{20} = +206$ (c=0.1, $CHCl_3$); MS: m/e 428 (M+): 396 (M—$CH_3OH$), 353 (M—$CH_3OH$—$CH_3CO$); NMR ($CDCl_3$): 3.51 (s, C-10-$OCH_3$); 4.66 (d, C-$10H$); 5.31 (q, C-$7H$), 13.6 and 14.07δ (s, OH phenolic).

9,10-Diepi-10-methoxydaunomycinone (VIII): m.p. 156° C. (dec.): MS: m/e (428 (M+); NMR ($CDCl_3$): 3.64 (s, C-10-$OCH_3$); 4.89 (s, C-$10H$), 5.12 (q, C-$7H$), 13.80 and 14.21δ (s, OH phenolic).

EXAMPLE 5

7,9-Isopropyliden-10-methoxydaunomycinone (XIV)

To a solution of 0.1 g. of 10-methoxydaunomycinone (VII) in 10 ml. of anhydrous dioxane there were added 5 ml. of 2,2-dimethoxypropane and a catalytic amount of p-toluenesulfonic acid. The reaction mixture was kept at 50° for 48 hours and then diluted with 50 ml. of chloroform. The thusly diluted solution was washed with an aqueous saturated solution of $NaHCO_3$, water and then dried over anhydrous $Na_2SO_4$. The crude residue, obtained by evaporation of the organic solvent, was chromatographed on a column of silicic acid using the mixture chloroform-acetone (95:5 v/v) as eluting agent. Pure 7,9-isopropyliden-10-methoxydaunomycinone (XIV) was obtained.

MS: m/e 468 (M+); 410 (M—$(CH_3)_2CO$); 378 (M—$(CH_3)_2CO$—$CH_3OH$); NMR ($CDCl_3$): 1.2 and 2.47 (s, $2CH_3$), 5.47δ (m, C-$7H$).

EXAMPLE 6

7-Methoxy-9,10-diepi-10-methoxydaunomycinone (XV)

Treatment of 9,10-diepi-10-methoxydaunomycinone (VIII) with 2,2-dimethoxypropane, as described in Example 5, afforded 7-methoxy-9,10-diepi-10-methoxydaunomycinone (XV). MS: m/e 442 (M+).

EXAMPLE 7

10-Methoxydaunorubicin hydrochloride (II)

To a solution of 0.43 g. (1 mmole) of 10-methoxydaunomycinone (VII) in 200 ml. of anhydrous methylene chloride were added 0.43 g. (1.2 mmoles) of 1-chloro-N,O-trifluoroacetyldaunosamine (IX). Then 0.32 g. (1.2 mmoles) of $AgSO_3CF_3$, dissolved in 26 ml. of anhydrous ether was added to the solution at room temperature with vigorous stirring over a period of 10 minutes. Finally, 0.2 ml. (1.4 mmoles) of anhydrous collidine was added to the reaction mixture. After 40 minutes, the mixture was treated with a saturated aqueous solution of $NaHCO_3$ and the separated organic phase was evaporated under vacuum. The resulting residue was dissolved in 100 ml. of methanol and kept at room temperature for 5 hours. The residue, which resulted from the removal of the solvent, was chromatographed on a column of silicic acid using the mixture chloroform-acetone (4:1 v/v) as the eluting agent. In addition to unreacted 10-methoxydaunomycinone (VII), there was also obtained 0.26 g. of pure 10-methoxy-N-trifluoroacetyldaunorubicin (I); m.p. 190° C. (dec.): TLC on Kieselgel plate $F_{254}$ (Merck) using the solvent system $CHCl_3$—$(CH_3)_2CO$ (4:1 v/v): Rf 0.3; NMR ($CDCl_3$): 1.30 (d, $CH_3$-CH); 3.52 (s, C-10 $OCH_3$); 5.30 (m, C-$7H$) and 5.53δ (m, C-1'-$H_ax$ WH=7 HZ). The compound (I); 0.26 g. was dissolved in 50 ml. of 0.1

N aqueous sodium hydroxide and after 30 minutes at 0° C., the solution was adjusted to pH 8.6 and repeatedly extracted with chloroform. The combined chloroform extracts, after being dried over anhydrous $Na_2SO_4$, were concentrated to a small volume and acidified at pH 4.5 with 0.1 N methanolic hydrogen chloride to allow crystallization of 10-methoxydaunorubicin (II), as the hydrochloride; m.p. 159° C. (dec.); $[\alpha]_D^{20°} +316°$ (c 0.05, $CH_3OH$); TLC on Merck Kieselgel $HF_{254}$ plate using solvent system $CHCl_3$—$CH_3OH$—$H_2O$ (13:6:1 v/v): Rf 0.37.

EXAMPLE 8

9,10-Diepi-10-methoxydaunorubicin (V)

The coupling reaction between 9,10-diepi-10-daunomycinone (VIII) and the halosugar, i.e., 1-chloro-N,O-trifluoroacetyldaunosamine (IX), as described in Example 7, yielded 9,10-diepi-10-methoxy-N-trifluoroacetyldaunorubicin (IV), which, after a mild alkaline treatment with 0.1 N aqueous sodium hydroxide for 30 minutes at 0° C., gave 9,10-diepi-10-methoxydaunorubicin, isolated as the hydrochloride (V), m.p. 140° (dec.); $[\alpha]_D^{20°} +252$ (C 0.05, MeOH).

EXAMPLE 9

10-Methoxydoxorubicin (III)

A solution of 10-methoxydaunorubicin (II) in a mixture of methanol and dioxane was treated with bromine to give the corresponding 14-bromoderivative which was subsequently treated with an aqueous solution of sodium formate at room temperature for 100 hours according to the technique disclosed in U.S. Pat. No. 3,803,124 to obtain 10-methoxydoxorubicin (III), isolated as the hydrochloride m.p. 195° (dec.) TLC on Merck Kieselgel $HF_{254}$ plate using solvent system $CHCl_3$—$CH_3OH$—H—$H_2O$ AcOH (8:2:0.6:1.4 v/v) Rf 0.45.

EXAMPLE 10

9,10-Diepi-10-methoxydoxorubicin (VI)

As in Example 9, by following the technique disclosed in U.S. Pat. No. 3,803,124, the treatment of 9,10-diepi-10-methoxydaunorubicin (V) with bromine and then with sodium formate, yielded 9,10-diepi-10-methoxydoxorubicin (VI) which was isolated as the hydrochloride.

BIOLOGICAL ACTIVITY

The compounds according to the invention were tested under the auspices of NCI - National Institute of Health, Bethesda, Maryland, against lymphocytic leukemia $P_{388}$ according to the procedure described in Cancer Chomotherapy Reports, part 3, vol. 3, page 9 (1972). The data reported in the table below show the antitumor activity of the new anthracycline derivatives.

TABLE

Antitumor activity of 10(R)-methoxydaunorubicin and 10(R)-methoxy-doxorubicin as compared with daunorubicin and doxorubicin

| Compound | Dose (mg./kg.) | T/C % |
|---|---|---|
| Danunorubicin | 16 | 90 |
|  | 8 | 98 |
|  | 4 | 119 |
|  | 2 | 124 |
| 10(R)-Methoxydaunorubicin | 12.5 | 133 |
|  | 6.25 | 115 |
|  | 3.13 | 110 |
| Doxorubicin | 16 | 108 |
|  | 8 | 171 |
|  | 4 | 133 |
|  | 2 | 129 |
|  | 1 | 119 |
| 10(R)-Methoxydoxorubicin | 50 | 104 |
|  | 25 | 115 |
|  | 12.5 | 127 |
|  | 6.25 | 125 |
|  | 3.13 | 108 |
| 9-cpi-10(S)-Methoxydaunorubicin | 50 | 126 |
|  | 25 | 132 |
|  | 12.5 | 110 |
|  | 6.25 | 102 |

The new compounds were tested in vivo on CDF mice infected with tumor cells. The i.p. injections were made on days 5, 9 and 13 (4 days interval between each injection) starting from fifth day after tumor transplantation in the mice. The median survival time expressed as percent of controls (T/C %) are reported.

Variations and modifications can, of course, be made without departing from the spirit and scope of the invention.

Having thus described our invention, what we desire to secure by Letters Patent and hereby claim is:

1. A compound of the formula:

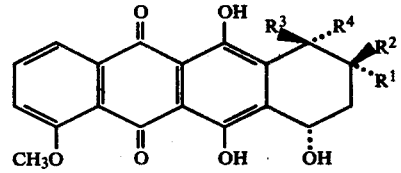

wherein $R^1$ is OH; $R^2$ is $COCH_3$; $R^3$ is $OCH_3$ and $R^4$ is H; or $R^1$ is $COCH_3$; $R^2$ is OH; $R^3$ is H and $R^4$ is $OCH_3$.

2. The compound having the formula:

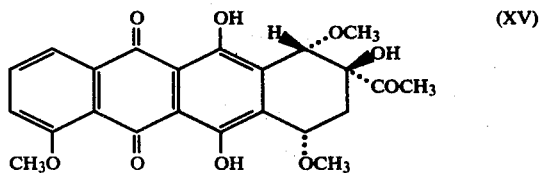

* * * * *

UNITED STATES PATENT AND TRADEMARK OFFICE
CERTIFICATE OF CORRECTION

PATENT NO. : 4,216,157
DATED : August 5, 1980
INVENTOR(S) : Sergio Penco, et al

It is certified that error appears in the above—identified patent and that said Letters Patent is hereby corrected as shown below:

Column 3, line 54:  "a" should read --$\alpha$--.

Column 6, line 3:  "a" should read --$\alpha$--.

Column 7, line 8:  "a" should read --$\alpha$--.

Column 7, line 55:  "Chomotherapy" should read -- Chemotherapy --.

Column 8, line 21:  "9-cpi" should read --9-epi--.

Signed and Sealed this

Second Day of June 1981

[SEAL]

Attest:

RENE D. TEGTMEYER

Attesting Officer

Acting Commissioner of Patents and Trademarks